United States Patent [19]
Cosgrove et al.

[11] Patent Number: 5,683,402
[45] Date of Patent: *Nov. 4, 1997

[54] FLEXIBLE SUTURE GUIDE AND HOLDER

[75] Inventors: Delos M. Cosgrove, Hunting Valley, Ohio; Than Nguyen, Huntington Beach, Calif.

[73] Assignee: Baxter International Inc., Deerfield, Ill.

[*] Notice: The portion of the term of this patent subsequent to Nov. 30, 2009, has been disclaimed.

[21] Appl. No.: 474,048

[22] Filed: Jun. 7, 1995

Related U.S. Application Data

[60] Continuation of Ser. No. 190,755, Feb. 2, 1994, Pat. No. 5,496,336, which is a division of Ser. No. 4,214, Jan. 13, 1993, Pat. No. 5,290,300, which is a continuation of Ser. No. 739,925, Aug. 2, 1991, abandoned, which is a continuation-in-part of Ser. No. 444,189, Nov. 30, 1989, Pat. No. 5,041,130, which is a continuation-in-part of Ser. No. 387,909, Jul. 31, 1989, abandoned.

[51] Int. Cl.$^6$ ............................................. A61B 17/00
[52] U.S. Cl. ........................................................ 606/150
[58] Field of Search ........................... 623/2, 900; 606/139, 606/148–150, 232, 233

[56] References Cited

U.S. PATENT DOCUMENTS

| | | | |
|---|---|---|---|
| 3,828,787 | 8/1974 | Anderson et al. | 623/2 X |
| 4,042,979 | 8/1977 | Angell | 623/2 |
| 4,364,126 | 12/1982 | Rosen et al. | 623/2 |
| 4,702,250 | 10/1987 | Ovil et al. | 606/148 |
| 4,759,758 | 7/1988 | Gabbay | 623/2 |
| 4,865,600 | 9/1989 | Carpentier et al. | 623/2 |
| 5,011,481 | 4/1991 | Myers et al. | 606/1 |
| 5,041,130 | 8/1991 | Cosgrove et al. | 623/2 |
| 5,290,300 | 3/1994 | Cosgrove et al. | 606/148 |

FOREIGN PATENT DOCUMENTS

| | | | |
|---|---|---|---|
| 0848024 | 7/1981 | U.S.S.R. | 623/2 |

*Primary Examiner*—David H. Willse
*Attorney, Agent, or Firm*—Raymond Sun; Debra D. Condino; Bruce Canter

[57] ABSTRACT

An assembly for holding a substantially flexible suture guide of predetermined length in a substantially taut position used to achieve a suture line having a dimension equal to the length of the suture guide, such as the circumference about a heart valve annulus. The assembly includes a rigid suture guide holder having a surface against which the length of suture guide is releasably positioned. The guide holder can have a shape or geometry, such as a circumference or circumferential segment, equivalent to the shape or geometry of the intended suture line. The shape of the guide holder can therefore be selected to hold the suture guide in the shape most advantageous to placing the desired suture line. The assembly further includes a mechanism for releasably binding the suture guide to the surface of the holder and a detachable handle extendibly attached to the holder by means of a lanyard so that the handle can be detached to afford an unobstructed view of the surgical site, but cannot be removed from the surgical site until the holder has also been removed.

32 Claims, 10 Drawing Sheets

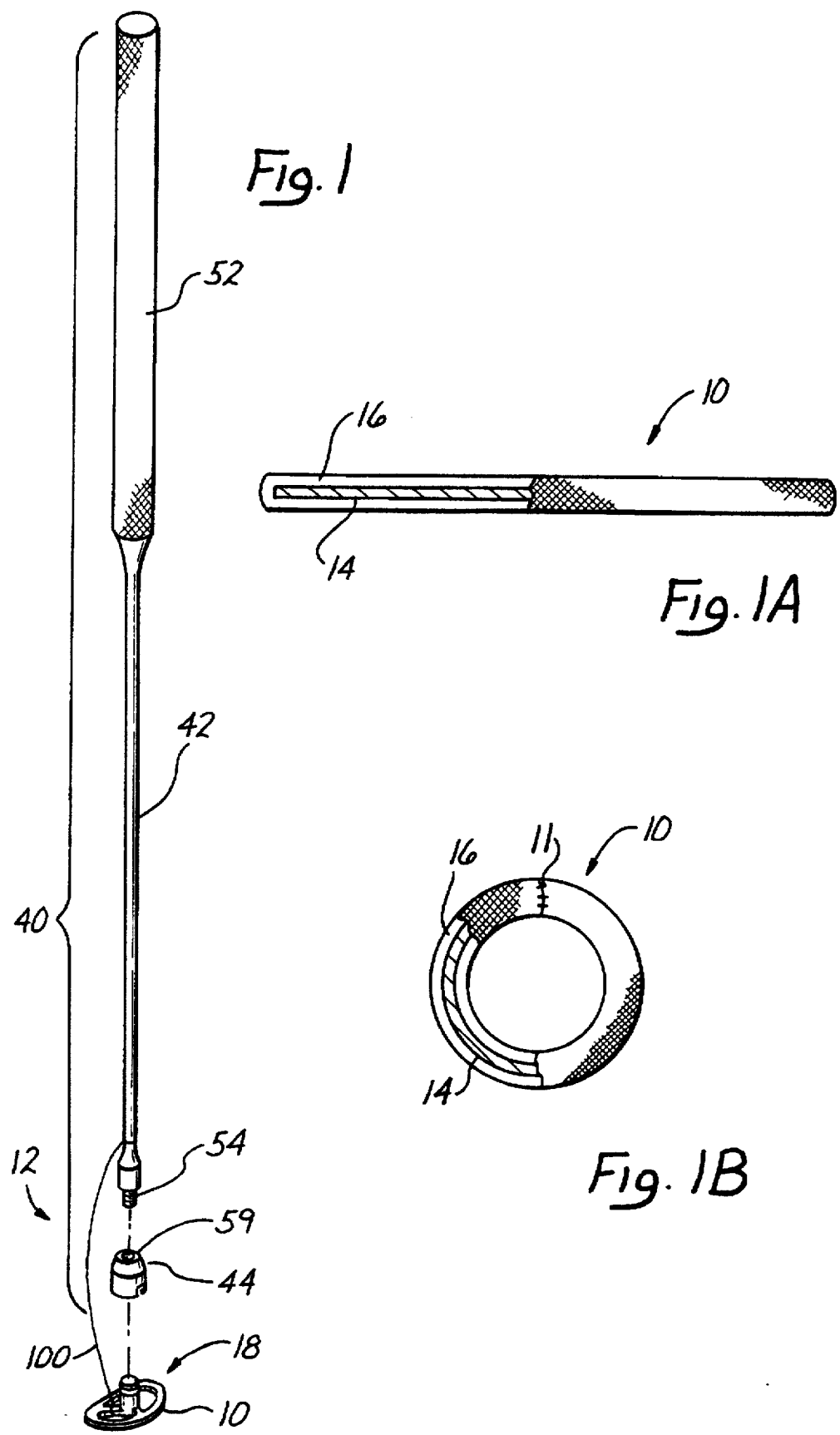

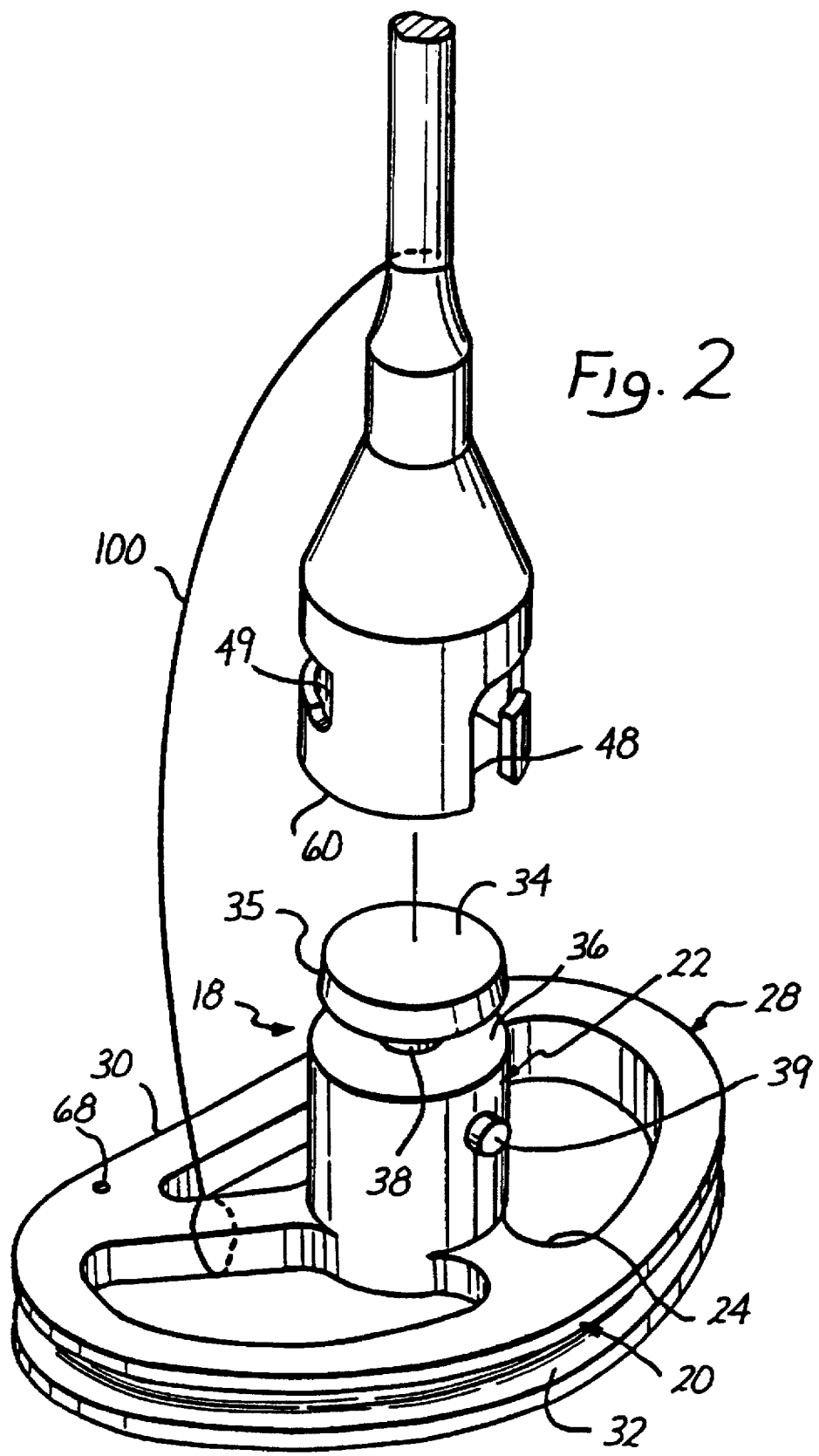

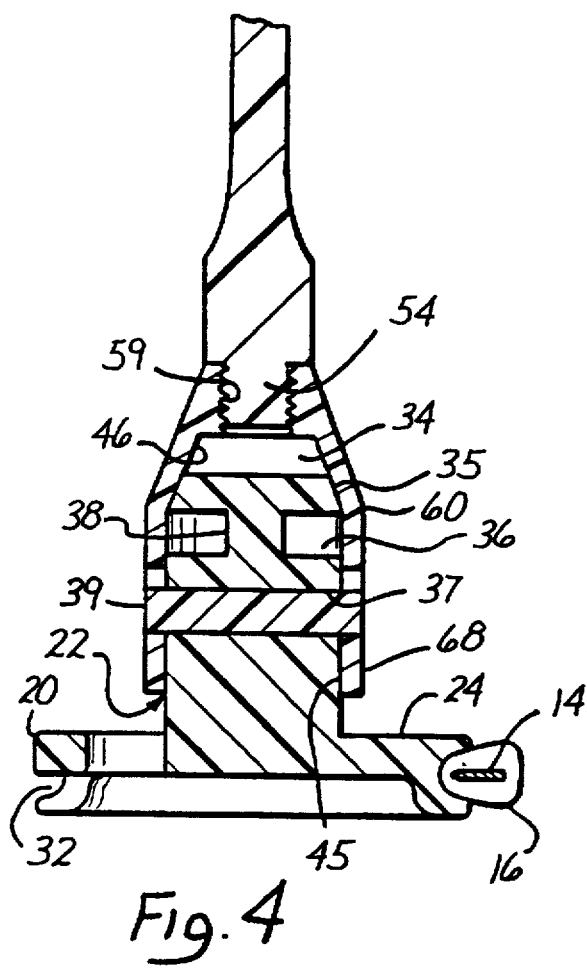
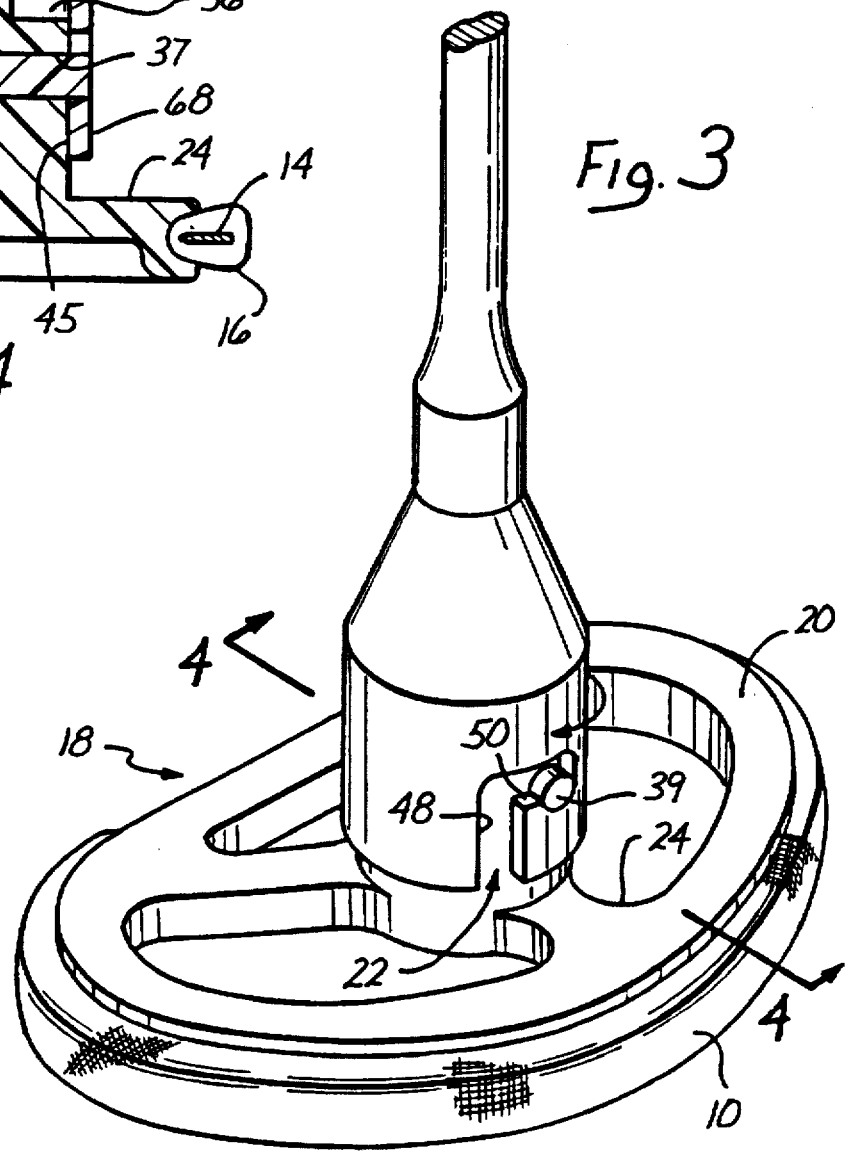

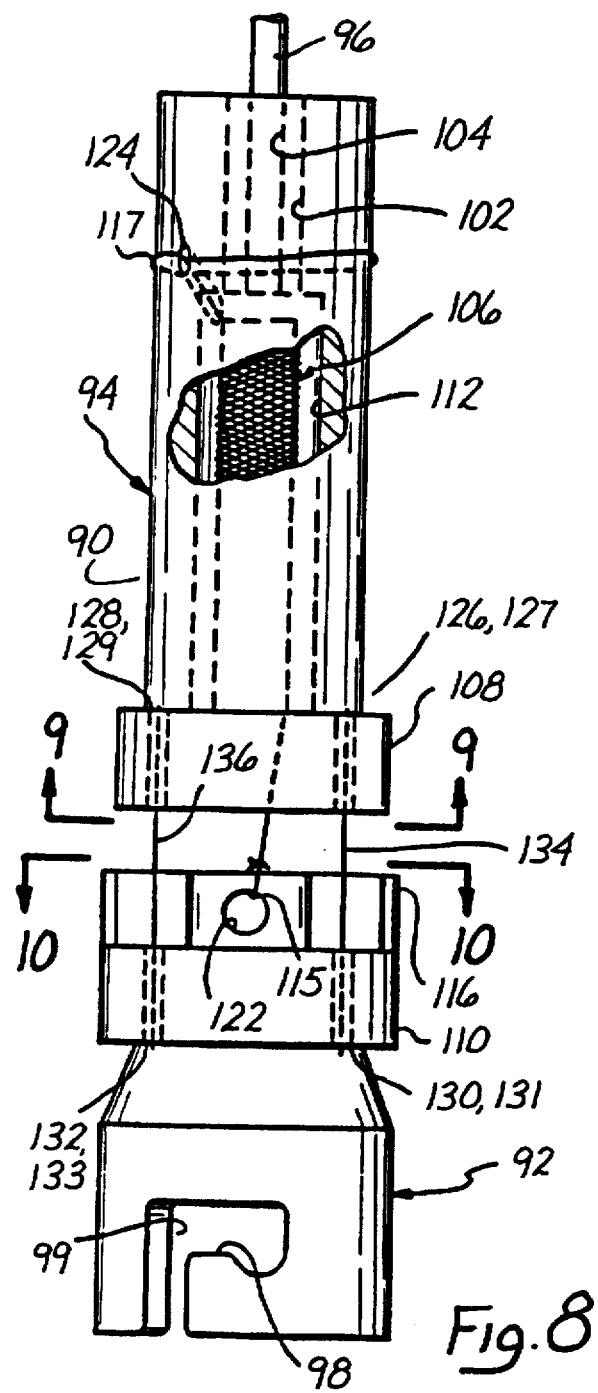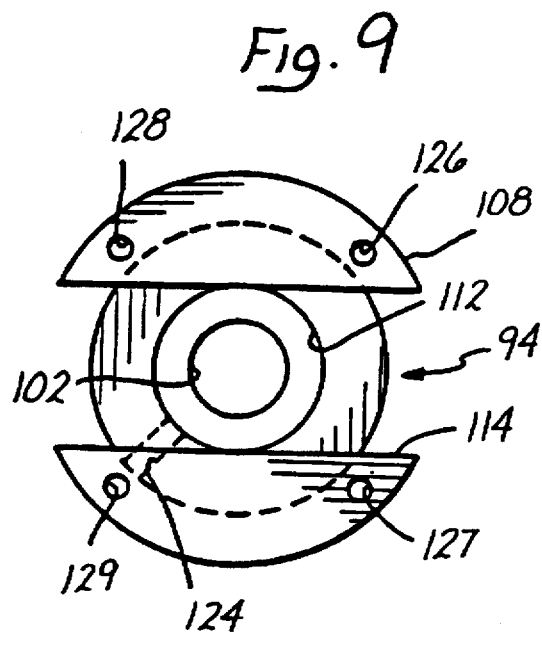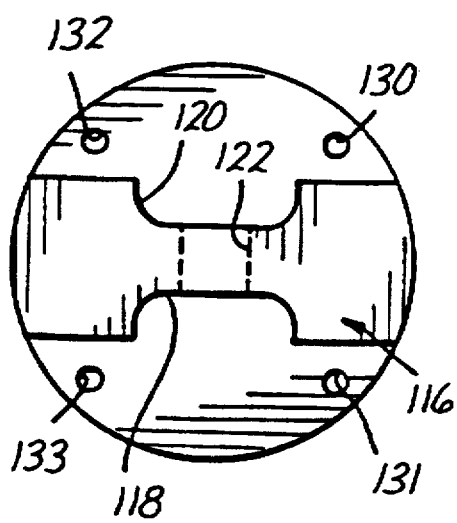

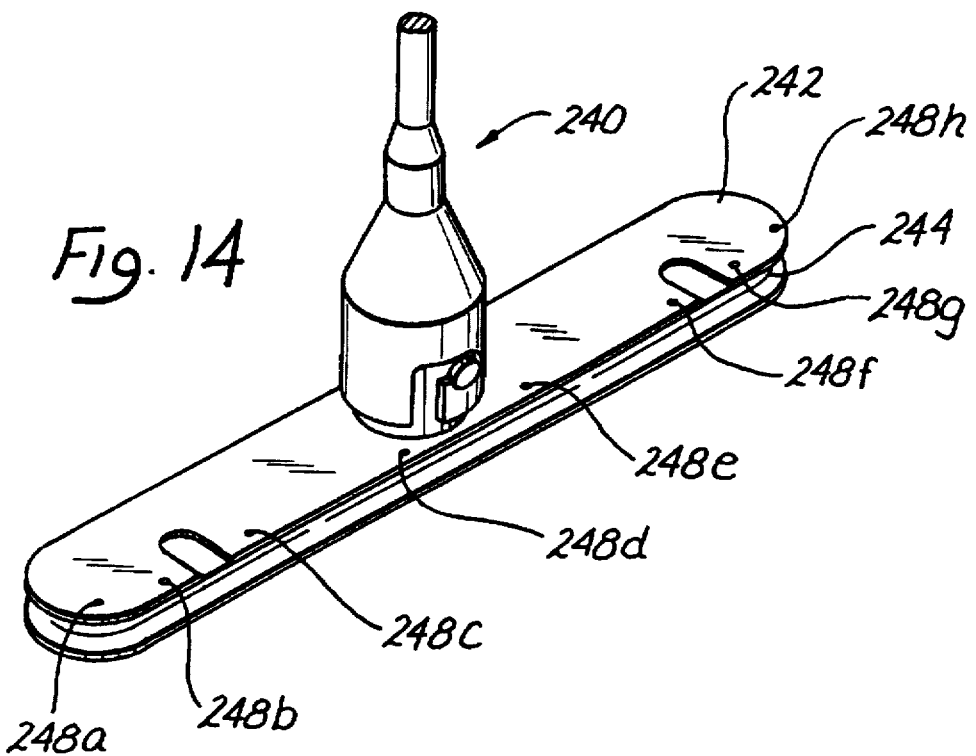
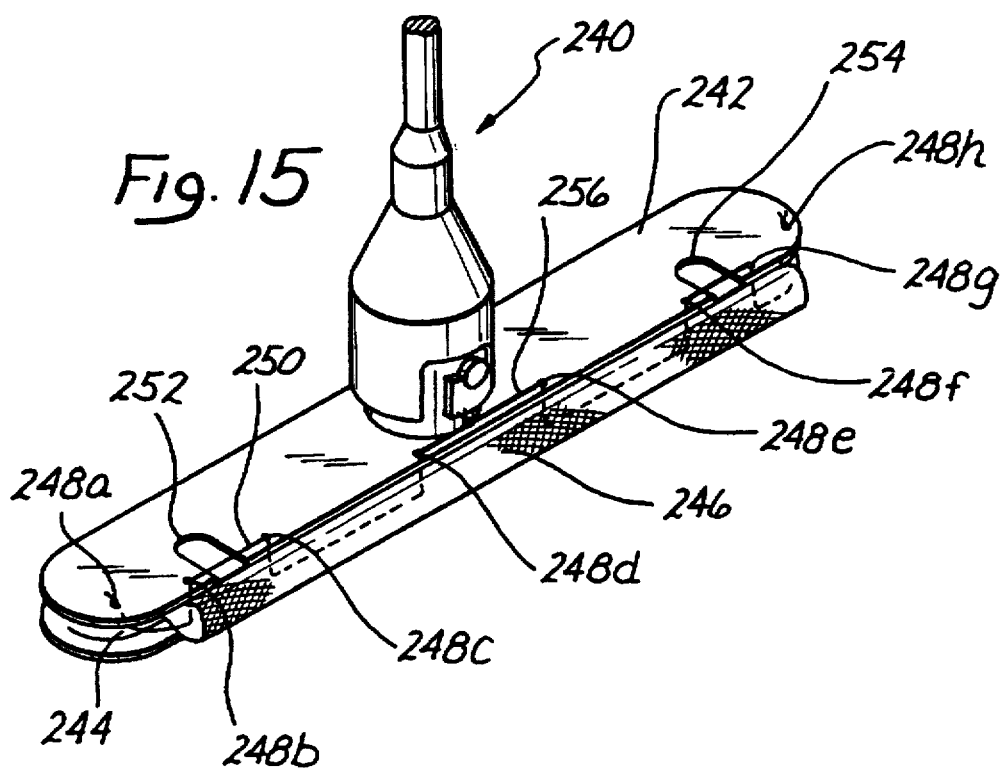

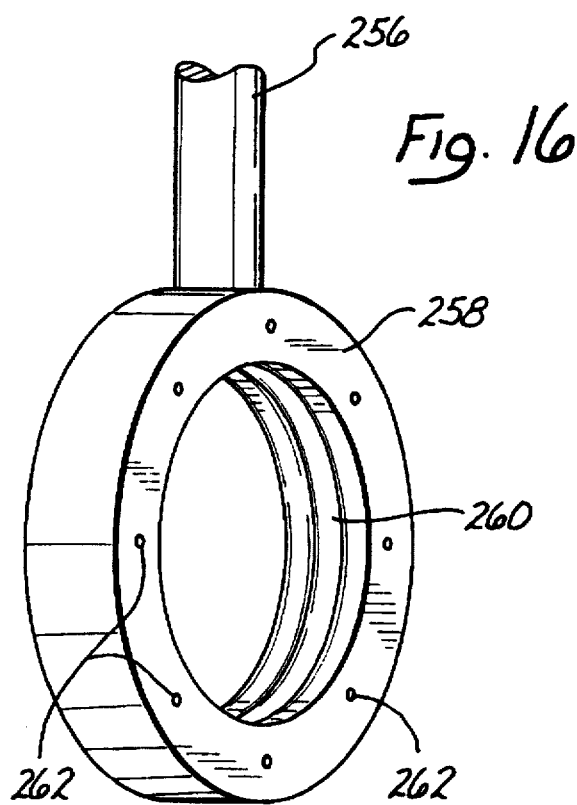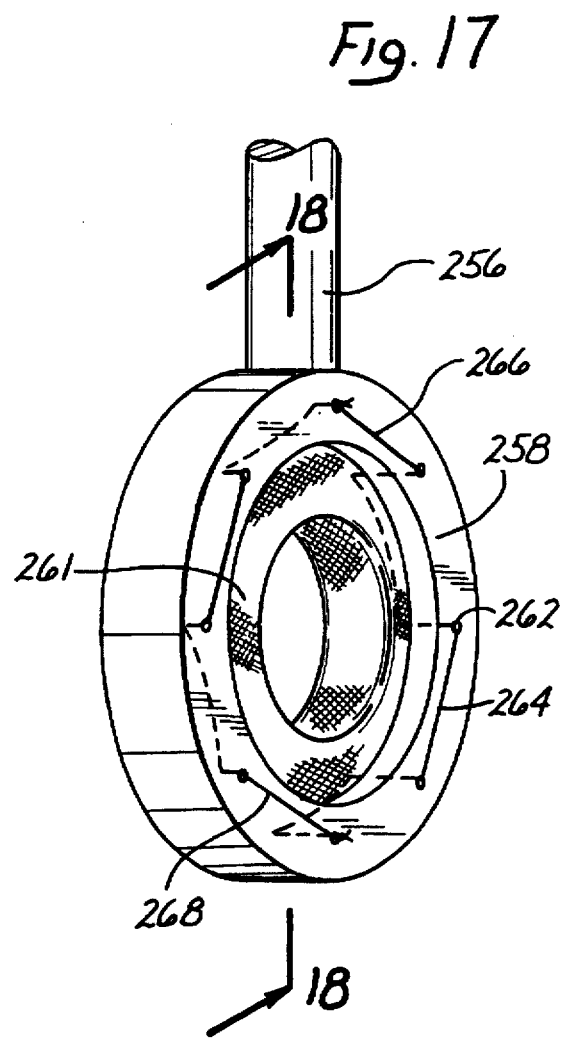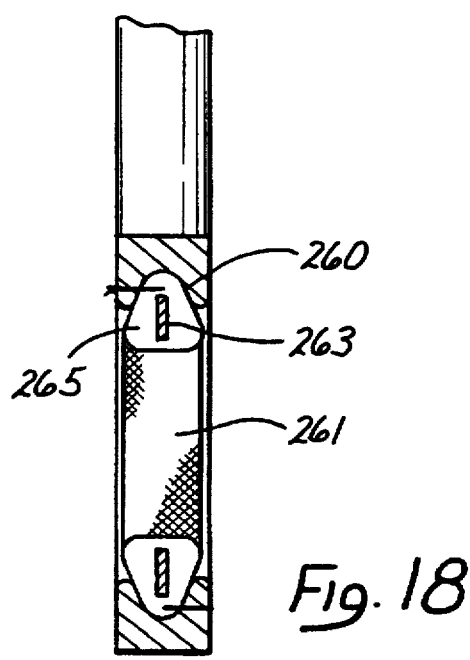

FLEXIBLE SUTURE GUIDE AND HOLDER

RELATED APPLICATIONS

This is a continuation of U.S. patent application Ser. No. 08/190,755, filed Feb. 2, 1994, now U.S. Pat. No. 5,496,336, which is a divisional of Ser. No. 08/004,214, filed Jan. 13, 1993, now U.S. Pat. No. 5,290,300, which is a continuation of U.S. patent application Ser. No. 07/739,925, filed Aug. 2, 1991, now abandoned, which is a continuation-in-part of U.S. patent application Ser. No. 444,189, filed Nov. 30, 1989, now U.S. Pat. No. 5,041,130, which is a continuation-in-part of U.S. patent application Ser. No. 387,909, filed Jul. 31, 1989, now abandoned. The present invention relates to a surgical suture guide used to control the dimension and/or shape of a suture line placed during surgical repair of an organ or body part. In particular, the present invention relates to a combination of a flexible suture guide releasably attached to a rigid holder for controlling the spacing and placement of surgical sutures.

BACKGROUND OF THE INVENTION

During surgical repair of an organ or other body part, the surgeon typically makes an incision to open the organ. Upon closure of the surgical wound, sutures are placed in the various layers of tissue to draw the two edges of the wound together so that the healing process can reform a smooth and competent surface. However, sutures often tear through the tissue if they are subjected to stress, thus damaging the surgical closure of the wound. It would be desirable in many instances to have a means for lending permanent support to strengthen and support the wall of the organ into which the surgical incision has been placed. Alternatively, in many instances it would be preferred to have a biodegradable suture guide.

In many cases, the incision is not a straight line, but is shaped to conform to an anatomical requirement, making it difficult for the surgeon to balance the tension on the sutures to form the desired shape. In a number of instances the suture line is substantially curvilinear and it is of utmost importance that the suture line maintain a predetermined dimension. For example, when two blood vessels, or other vessels, such as intestines, are sutured together, the need exists for some means of preventing the suture line from constricting the vessel so as to create a potential point of blockage. Similar problems arise during bowel and bronchial resection. As another example, when the surgeon is reducing the size of a stomach by surgical means, the need exists for a means to assure that the reshaped organ will have a particular circumferential dimension and that the pleats used to reduce the size of the organ are evenly distributed so as to avoid formation of areas of reduced flexibility along the suture line. In other situations, such as in cosmetic surgery, the surgeon may desire to assure that the suture line is limited to a predetermined length.

In all of these situations, it is desirable to use a suture guide to aid the surgeon in achieving the desired dimension of the surgical closure and/or to rigidly support the area where the sutures are placed, thus avoiding the danger that the sutures will tear through the tissue or that the suture line will act like a draw string and undesirably bunch up the tissue.

These problems are particularly acute in the surgical procedure known as annuloplasty wherein any of a number of types of prostheses have been used in surgical correction of deformed mitral or bicuspid heart valves.

Diseases and certain natural defects to heart valves can impair the functioning of the cusps of the valves in preventing regurgitation of blood from the ventricle into the atrium when the ventricle contracts. For example, rheumatic fever and bacterial inflammations of the heart tissue can distort or dilate the valvular annulus, thus resulting in displacement of the cusps away from the center of the valve and causing leakage of blood during ventricle contraction.

Two techniques, generally known as annuloplasty, are used to reshape the distended and/or deformed valve annulus. In the technique known as "plication," the circumference of the valve annulus is reduced by implanting a rigid or semi-rigid prosthetic ring of reduced circumference about the base of the annulus while the annulus is pleated to reduce its circumference to that of the ring. In the technique known as "reconstruction", the circumference of the annulus is not reduced, but the annulus is restructured into an elongate shape. To accomplish this goal, a rigid or semi-rigid ring having the same circumference as the annulus but in an elongate or elliptical shape is surgically implanted about the base of the valve. Both plication and restructuring are intended to eliminate the gap in the closure of the distended valve by bringing back together the tips of the valve cusps.

Many different types of prostheses have been developed for use in annuloplasty surgery. In general, prostheses are annular or partially annular shaped members that fit about the base of the valve annulus. Initially the prostheses were designed as rigid frame members, or "rings", of metallic or other rigid materials that flex little, if at all, during the normal opening and closing of the valve. Since a normal heart valve annulus continuously flexes during the cardiac cycle, a rigid ring prosthesis interferes with this movement and thereby restricts movement of the valve itself. Sutures used to implant rigid ring prostheses consequently undergo stresses sufficient to tear the sutures loose. Examples of rigid annuloplasty ring prostheses are disclosed in U.S. Pat. Nos. 3,656,185, issued to Carpentier on Apr. 18, 1972; and 4,164,046, issued to Cooley on Aug. 14, 1979.

Others have suggested the use of completely flexible annuloplasty ring prostheses. Examples of completely flexible ring prostheses are disclosed in U.S. Pat. No. 4,290,151, issued to Massana on Sep. 22, 1981, and are discussed in the articles of Carlos D. Duran and Jose Luis M. Ubago, "Clinical and Hemodymanic Performance of a Totally Flexible Prosthetic Ring for Atrioventricular Valve Reconstruction", 5 *Annals of Thoracic Surgery*, (No. 5), 458–463, (November 1976) and M. Puig Massana et al, "Conservative Surgery of the Mitral Valve Annuloplasty on a New Adjustable Ring", *Cardiovascular Surgery* 1980, 30–37, (1981).

Flexible prostheses generally include an inner support member formed from a flexible material. This support member is wrapped in woven, biocompatible cloth material. Realignment of the valve cusps during opening and closing of the valve is obtained by the proper suturing of the ring about the valve annulus. However, completely flexible ring prostheses provide almost no support to the suture area during the precarious implant procedure. Even though the surgeon attempts to evenly distribute the sutures along the periphery of the valvular annulus, during implant the drawstring effect of the sutures tends to bunch the material covering the flexible ring so that the sutures also bunch together at localized areas around the ring. This phenomenon, known as multiple plications in the heart valve annulus, causes rigid areas around the annulus. Thus, the flexible ring actually ends by imparting areas of rigidity and thereby distorts the valve annulus during the opening and closing of the valve despite the desired reduction in circumference of the valvular annulus.

To overcome some of the drawbacks of rigid ring prostheses, still further types of annuloplasty prostheses have been designed to allow for adjustment of the ring circumference, either by the surgeon during implant, or automatically as the implanted ring moves during the opening and closing of the valve. This type of adjustable prosthesis is typically designed in combination with a rigid, or at least partially rigid, frame.

An example of a self adjusting ring prosthesis is taught in U.S. Pat. No. 4,489,446, issued to Reed on Dec. 25, 1984. To provide for self adjustment of the prosthetic annulus, two reciprocating rigid metal pieces form the frame. U.S. Pat. Nos. 4,602,911, issued to Ahmadi et al. and 4,042,979, issued to Augell on Aug. 23, 1977, provide further adjustable ring protheses having a mechanism for adjusting the circumference of the ring. But due to rigidity of the frame members, the self-adjusting prostheses do not overcome many of the disadvantages of other types of rigid ring prostheses.

U.S. Pat. No. 4,055,861, issued to Carpentier on Nov. 1, 1977, teaches an annuloplasty ring prosthesis having a flexibility between the completely flexible rings discussed above and the various types of rigid ring. The ring of Carpentier is deformable to an equal degree and simultaneously in all directions and preferably has the elasticity of an annular bundle of 2 to 8 turns of a cylindrical bristle of poly(ethylene terephthalate).

While rigid and semi-rigid annuloplasty rings eliminate the bunching caused by flexible rings, the restrictive nature of such rings is generally detrimental to the valve's ability to open and close normally. It thus remains an object of the invention to provide a surgical means for reshaping a deformed or dilated heart valve annulus having none of the above described drawbacks associated with known annuloplasty ring prostheses.

For use in annuloplasty of heart valves, as in other applications, it is desirable that a suture guide be entirely flexible, light weight, and compliant while having sufficient strength to withstand stress placed upon the sutures sewn through and around it. However, an entirely flexible suture guide cannot prevent bunching of the tissue in the drawstring effect described above and thus cannot assure that the suture line and the tissue into which it is placed will maintain any desired dimension, for example, a desired circumference. Therefore the need exists for a means of temporarily providing rigidity and fixed dimension to the suture guide during the surgery, but rendering the suture guide freely flexible once the surgery has been accomplished.

DESCRIPTION OF THE DRAWINGS

The present invention may be better understood and the advantages will become apparent to those skilled in the art by reference to the accompanying drawings, wherein like reference numerals refer to like elements in the several figures, and wherein:

FIG. 1 is a perspective exploded view of a flexible suture guide mounted on a rigid holder assembly in accordance with an embodiment of the invention FIG. 1A is a top view in partial cross-section of a length of a flexible suture guide in accordance with the present invention.

FIG. 1B is a top view in partial cross-section of the flexible suture guide of the present invention sutured into a ring configuration.

FIG. 2 is an exploded view of the guide mount portion and lower part of the handle portion of the holder assembly of FIG. 1 without the suture guide.

FIG. 3 is a perspective view of a flexible suture guide of the present invention mounted on the assembled guide mount and lower handle portions seen in FIG. 2.

FIG. 4 is a cross-sectional view of the assembled guide mount and lower handle portions of FIG. 3 along line 4—4.

FIG. 7 is a cross-sectional view of a suture guide having a lenticular cross-sectional shape in accordance with another embodiment of the invention.

FIG. 8 is a side perspective sectional view of a handle assembly in accordance with another embodiment of the invention.

FIG. 9 is a bottom view of the handle extension of FIG. 8.

FIG. 10 is a top view of the housing of FIG. 8.

FIG. 14 is a perspective view of a linear suture guide holder in accordance with another embodiment of the invention.

FIG. 15 is a perspective view of the suture guide holder of FIG. 14 with a suture guide attached.

FIG. 16 is a perspective view of a circular suture guide holder in accordance with another embodiment of the invention.

FIG. 17 is a perspective view of the suture guide holder of FIG. 16 with a suture guide attached.

FIG. 18 is a cross-sectional view of the suture guide and holder of FIG. 17 taken along line 18—18.

SUMMARY OF THE INVENTION

Figure 5:
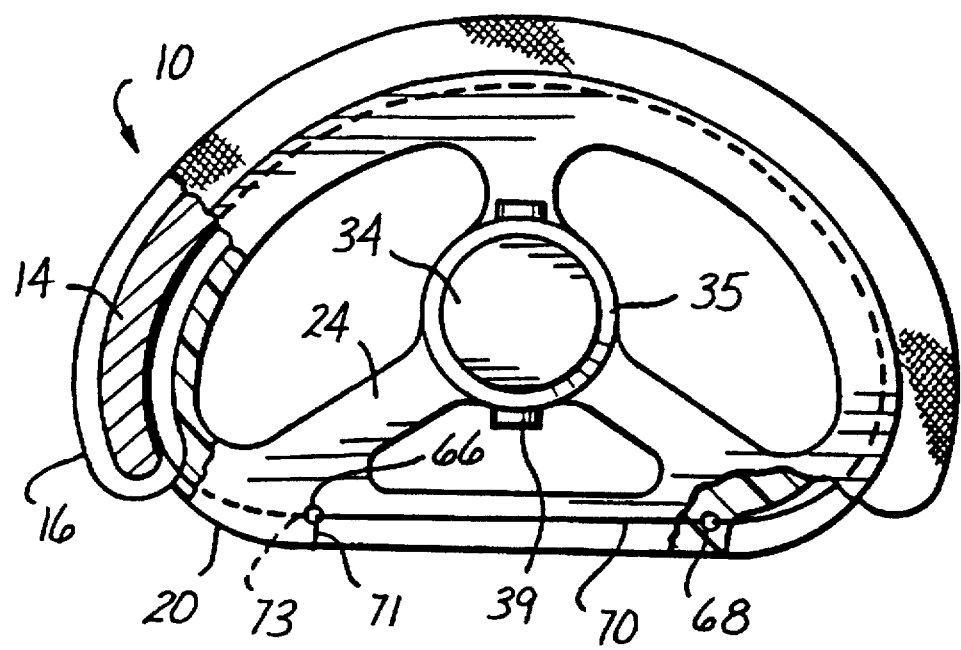
FIG. 5 is a top view of the guide mount seen in FIG. 3 with a flexible suture guide tautly secured thereto.

The present invention overcomes the above discussed disadvantages by providing an assembly for holding a substantially flexible suture guide in a substantially taut position for placing a suture line having a predetermined dimension. When attached to the holder assembly, the flexible suture guide assumes a shape or geometry, such as a circumference, that conforms to the shape or geometry of that portion of the body organ or vessel that is being sutured. The holder assembly can be formed to hold the suture guide in any desired shape, whether straight, curvilinear, or a combination of the two and the suture guide can be either biodegradable or permanently implantable. Thus the surgeon undertaking reconstructive surgery is aided in achieving a suture line of any desired shape, geometry and/or dimension.

The assembly includes a holder portion having a surface against which the suture guide is positioned and held tautly in a fixed shape, geometry and/or dimension. More particularly, the holder assembly includes a body having an outwardly facing surface, generally flat, against which the suture guide is tautly positioned so that the suture guide assumes the shape, geometry and/or dimension desired for the suture line. Preferably, this surface is formed with at least one depression for receiving a portion of the suture guide. The assembly further includes a detachable handle and a mechanism for releasably binding the suture guide to the surface.

The flexible suture guide used with the assembly of the invention comprises a generally elongated flexible body element having an internal flexible rib encased within a biocompatible covering, such as a woven cloth material. The suture guide can be formed of either biodegradable or non-biodegradable materials depending upon whether its purpose is to serve as a permanent support to prevent tearing out of the sutures placed through it or whether the suture-supporting function is to be a temporary one. In addition to its function as a post-surgical support for sutures, during surgery when used in combination with the holder disclosed herein, the suture guide serves as a rigid support and template by which the surgeon controls the length of the finished suture line. For instance, if the task is to suture together two ends of a bowel from which a section has been removed, the combination of suture guide and holder assure that the circumference of the surgical jointure is substantially similar to the circumference of the nearby regions of the colon, rather than smaller or larger.

Therefore, the holder device is designed to lend a temporary rigidity or tautness to the suture guide while lending to it a shape selected to facilitate the suturing task. For instance, when the task is to place a line of sutures around the circumference of a curvilinear surface, the holder is designed to fit around at least a portion of the circumference while holding the suture guide against the said circumference to aid the surgeon in making a surgical jointure that does not distort the said circumference.

In use, the suture guide is releasably retained against the outwardly facing body surface by a means for releasable attachment, for example one or more threads, pieces of Velcro™, and the like, placed so that the suture guide lies along and temporarily substantially assumes the shape of the body. The means for attachment may also be a biodegradable adhesive having the capacity to firmly attach the suture guide to the holder body for sufficient time to complete the surgery, but having the capacity to dissolve or be dissolved once the suture line has been placed. In one embodiment, the thread attaches the suture guide to the body surface at least at two points, for example at its extreme ends, by passing at least partially through the suture guide and about the body, i.e., by means of an in and out stitch or stitches.

The means for releasable attachment of the suture guide to the body must be such that the suture guide can be released from the body once the suture line has been placed by the surgeon without disturbing the sutures sufficiently to cause dislocation or tearing of the sutures through the tissue. For example, if the means for releasable attachment is one or more threads, a portion of the thread(s) affixing the suture guide to the body can be positioned to be cut by scissors, or the like, to freely release the suture guide from the body. When the thread or threads are cut or otherwise ruptured, the suture guide is freely released from the body.

DESCRIPTION OF THE PREFERRED EMBODIMENTS

The present invention is directed to a holder assembly for holding a substantially flexible, implantable suture guide in a substantially taut position for suturing along a suture line having a desired shape or dimension, such as the desired circumference to which an enlarged heart valve annulus is to be reduced by the formation of pleats about the base of the, valve annulus. The suture guide of the invention is formed from a freely flexible rib encased within a woven cloth covering. In use, the flexible suture guide of the invention is held taut by the holder assembly and in a configuration determined by the shape of the holder assembly while the surgeon uses the support provided by the taut suture guide to evenly place the sutures and to draw the tissue by means of the sutures passed through the suture guide into a suture line having a shape substantially similar to that of the suture guide and holder. For example, for use in annuloplasty, the holder assembly can be C-shaped so that the suture guide temporarily affixed thereto assumes a C-shaped configuration. The suture guide can then be sutured to the base of a heart valve annulus so as to restrict the circumference of a dilated and/or deformed valve annulus to a more normal one. When the suture guide is released from the holder, it will assume any shape that that portion of the body organ or vessel assumes in accordance with the dynamic function of the organ or vessel.

Generally the guide mount assembly includes a guide support formed with a shape similar to that of the desired suture line, as in the above example wherein the holder assembly is in the general shape of the valve annulus about which the suture guide is to be surgically placed to assist in holding pleats in the walls of the annulus. The suture guide is mounted along at least a portion of this guide support, for example along a straight or a curved portion.

The holder assembly allows the surgeon to properly position the suture guide while the suture guide is used to draw the sutures and associated tissue into the desired configuration during the suturing process. The freely flexible suture guide is given temporary rigidity during surgery by the detachable holder assembly, thus lending precision to the surgeon in controlling the placement and location of the stitches in the suture line. In an annuloplasty, for example, the potential for forming multiple plications as the circumference of the valve annulus is adjusted is thus greatly reduced.

Referring now to FIG. 1A, the suture guide 10 is an elongate, flexible member of a predetermined dimension. Due to its flexibility, the length of suture guide 10 can be manipulated to assume any desired shape, ie., circular, C-shaped, straight, curvilinear or a combination of curvilinear and straight segments. In FIG. 1B, suture guide 10 is shown as shaped into a ring by suturing the two ends together with sutures 11. As shown in FIG. 1A, suture guide 10 comprises a substantially flexible inner rib 14 encased within covering 16.

Rib 14 comprises a flat, rod-like or tubular piece of biocompatible resilient, flexible material, such as mylar or silicone rubber. Rib 14 can also contain a substance opaque to x-rays, for example, about 10 to 15 weight percent, preferably 13 weight percent, of barium sulfate so that the location of the suture guide can be determined in post-operative x-rays. The outer covering 16 is formed from any biocompatible material having sufficient strength to serve as an anchor to sutures without tearing and sufficient flexibility to be formed into a tight covering for rib 14 without restricting flexibility of suture guide 10. Preferably, the outer covering 16 is a woven cloth having a nap to encourage tissue ingrowth, for example a dacron velour. This outer covering 16 is tightly wrapped and sewn about frame 14 so as to completely encase it. The thickness of the outer cloth 16 is sufficient to allow the surgeon to pass a suture therethrough.

FIG. 1 shows an exploded view of one embodiment of a holder assembly to which a suture guide is mounted, as seen generally at 12 and 10 respectively. The holder assembly 12 includes a guide mount assembly 18 and handle assembly 40 comprising a handle 42 and housing 44.

FIGS. 2 through 5 illustrate, in greater detail the guide mount assembly 18 and how the suture guide 10 is mounted thereon. Guide mount assembly 18 includes a guide support 20. For illustrative purposes, the suture guide assembly 18 here shown is one intended for use in plication of a distended heart valve annulus. Therefore facing edge of guide support 20 is generally C-shaped or annular, having a shape and circumferential dimension similar to that the surgeon desires to achieve in the human heart annulus by means of annuloplasty surgery. More particularly, support 20 is generally lenticular, having a C-shaped portion 28, with its ends connected by a straight side 30.

The suture guide 10 is fitted into a groove or trough 32 located about the curved C-shaped portion 28 of the guide support 20 Trough 32 is dimensioned to receive a portion of the suture guide 10, as best seen in FIG. 4. The positioning of the suture guide 10 within the trough 32 conforms guide 10 to the shape of the guide support 20 while exposing a substantial portion of the covering 16 outside of the trough 32 to allow the surgeon to pass a suture therethrough.

In the embodiment shown in FIGS. 2–5, the guide mount assembly 18 also includes a central support hub 22 to which the guide support 20 is attached by a multiplicity of integrally formed spokes, preferably three, one of which is seen at 24. The arrangement of mount assembly 18 including, in this instance, a curved guide support 20 with hub 22 and spokes 24, allows the surgeon to visually observe the heart valve during the suturing process. Central support hub 22 is formed with an annular groove 36. This groove 36 is formed proximate that end 34 of hub 22 opposite guide support 20, and defines a post member 38. That portion of hub 22 remaining on the side of the groove 36 opposite the guide support 20, and hub end 34, includes an inwardly tapering peripheral surface, as seen generally at 35. The hub 22 also includes an open bore 37 through which is fitted a cylindrical plug 39. The plug 39 is dimensioned to extend out from both sides of the bore 37. The purpose of tapered surface 35, and the plug 39 will be described hereinafter.

As is further seen in FIG. 1, the handle assembly 40 includes an elongated handle 42 having end 54 mounted to housing 44. While housing 44 may be integrally formed at the end 54 of the post 42, preferably end 54 is formed with outwardly facing threads that threadably mate with threads formed along a surface of an opening 59 formed in the top of the housing 44. The opposite end of post 42 is formed with an external etched surface 52 to assist the surgeon in gripping post 42. In another embodiment, end 54 of post 42 and opening 59 of housing 44 can be formed so that end 54 can be press fit into opening 59.

Housing 44 is a thimble-shaped structure having a circular wall 60 defining a cavity 46. As seen better in FIG. 4, cavity 46 is open at one side, seen generally as opening 45. The inner surface of the circular wall 60 inwardly converges a short distance from the opening 45. The cavity 46 is generally wide enough at the open side 45 to snugly receive hub 22, but the plug 39 extends sufficiently outward from hub 22 to prevent passage through open side 45 into cavity 46. Wall 60 is formed with two J-shaped notches, seen at 48 and 49 in FIGS. 2 and 3. These J-shaped notches 48 and 49 are formed and positioned to respectively receive the ends of the plug 39 extending outward from the hub 22. The shape of the notches 48 and 49 defines a landing 50 between the long and short legs of each notch.

Handle assembly 40 is coupled to the guide mount assembly 18 by inserting end 34 of the hub 22 into the cavity 46, with one of the outwardly extending ends of the plug 39 passing through a respective one of the J-shaped notches 48 and 49. The tapered surface 35 of the hub 22 engages the inwardly tapering surface of the wall 60. This causes a slight compression of the hub end 34, resulting in a spring force. The spring force acts to restrain the movement of the outwardly extending ends of the plug 39 through the larger legs of the J-shaped notches 48 and 49. Additional exertion moves the ends of plug 39 through the larger legs of J-shaped notches 48 and 49, with rotation of handle 40 passing the outward ends of plug 39 across the landings 50 and into the smaller leg of the J-shaped notches 48 and 49.

The spring force established by the slight compression of the hub end 34 maintains the coupling between housing 44 and guide mount assembly 18. The handle 40 is decoupled from the guide mount assembly 18 by reversing the described procedure.

One embodiment of the means for releasably attaching suture guide 10 to guide support 20 of guide mount assembly 18 is seen in FIG. 5. Guide support 20 is formed with two apertures 66 and 68 extending through guide support 20 and communicating with groove 32. The exact positioning of apertures 66 and 68 is not critical. As illustrated, apertures 66 and 68 are formed along the straight portion of guide support 20, at a location proximate two of the spokes 24.

One end 71 of a cord or suture thread 70 is passed through one of the apertures, as illustrated hole 66, and tied off on guide support 20. The other end 73 of suture 70 is passed through the body of suture guide 10 from one end to the other. This end 73 is then passed first through hole 68 and then through and tied off at hole 66. After suture guide 10 is sutured into position during surgery, i.e., about the valve annulus, that portion of the suture 70 between apertures 66 and 68 is snipped or cut in two. Suture 70 passes out of suture guide 10 by withdrawing the holder assembly 12.

In accordance with another embodiment (not shown), the first end 71 is tied off at hole 66, with the second end 73 passed first through one end of the suture guide 10, and then brought back across and passed through the other end of suture guide 10, through hole 68 and again tied off at hole 66. Removal of suture 70 is accomplished by snipping the suture in two at any point between the two holes and withdrawing it.

Figure 6:
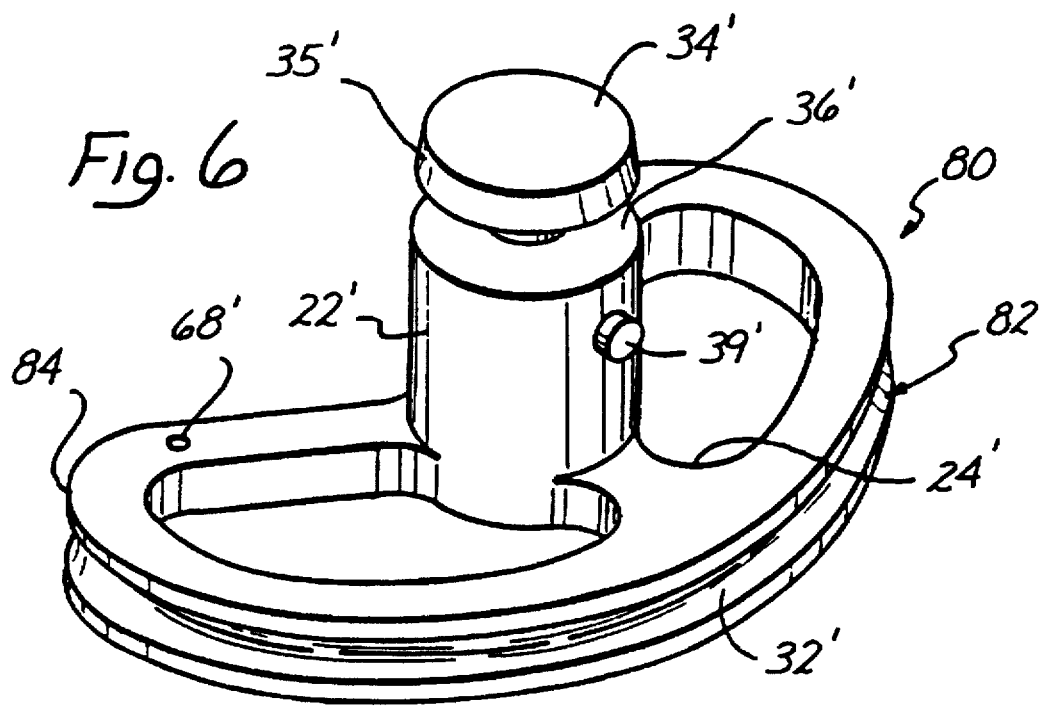
FIG. 6 is a perspective view of a guide mount in accordance with another embodiment of the invention.

An alternative embodiment of the guide mount assembly 80 as seen in FIG. 6 includes a guide support 82 having an open C-shaped side 84 but no straight side joining the ends of the C. Except for the stated difference in shape of the guide support 82, guide mount assembly 80 in FIG. 6 includes elements similar to those described for the suture guide of FIG. 5 (as is indicated by the prime of the previously provided element number), and will be described in no further detail herein. In this embodiment of guide mount assembly 80, the means for releasably attaching the suture guide to the guide support is a suture (not shown) positioned by tying off as described above across an open space between holes 68' and 66' (not shown).

In a preferred embodiment of the invention, the handle assembly 40 is tethered to the guide mount assembly 18. As seen in FIG. 1, this tethering is performed by connecting one end of a lanyard, seen generally at 100, to the handle assembly 40 and the other end of the lanyard 100 to the guide support 20, for instance to one of spokes 24. Lanyard 100 allows a surgeon to detach the handle assembly 40 from the guide support 20 during the suturing procedure to gee a clearer view of the surgical site. By tethering handle 40 to the guide mount assembly 18, the risk of the surgeon leaving the guide support 20 in the patient after completion of the surgical procedure is greatly reduced. Lanyard 100 also allows the surgeon to easily remove the guide support 20 after the handle has been detached.

In a still further preferred embodiment, a handle assembly 40 is modified to house a spool of suture or string that acts like a tether for the guide mount assembly. The tether is attached at opposite ends to the handle assembly and the guide mount assembly respectively and automatically spools out of the handle assembly when the handle is disconnected from the guide mount assembly.

This preferred embodiment is better seen in the several FIGS. 8 through 10. The lower portion of a handle assembly in accordance with this embodiment is seen in FIG. 8 at 90. Handle assembly 90 includes a housing 92, a handle extension 94, and a handle post 96.

Housing 92 includes a pair of opposing J-shaped notches 98 and 99 that function similarly to the J-shaped notches 48 and 49 described above. The handle extension 94 is fastened to the lower end of the handle post 96 in any suitable manner. As shown, the handle extension 94 includes at one end a bore 102 for receiving the lower end 104 of the handle post 96. End 104 of the handle post may be held in bore 102 by welding, stamping, or by providing the respective members with interlocking threaded surfaces. Accordingly, neither of these structures of the handle assembly 90 will be discussed in any greater detail.

The main distinction to the previously described embodiment is that the handle assembly 90 is formed to carry a spool of suture, seen generally at 106. This suture spool 106 is housed in a bore 112 formed in the handle extension 94. Handle extension 94 and housing 92 are formed to releasably fit together. Handle extension 94 and housing 92 include mating collars 108 and 110, respectively. Collar 108 is formed with a groove 114 that receives a tongue 116 extending upward from collar 110. Tongue 116 is formed with a central aperture 122, and two opposing cut-aways 118 and 120 that extend out in opposite directions from this aperture 122.

Each of the collars 108 and 110 possesses four apertures. Apertures 126–129 of collar 108 align with apertures 130–133 of collar 110 when the handle extension 94 and housing 92 are fitted together.

Suture spool 106 comprises a length of suture wound into a cylindrical configuration along lower end 104 of handle post 96, which fits into bore 112. The opposite ends of this suture length are tied to the tongue 116 and the handle extension 94. One end of the suture is drawn through the central aperture of 122 and tied to tongue 116, as seen at 115. The opposite end of the suture is drawn through an opening 124 extending from the bore 112 through the handle extension 94 and is tied around the handle extension 94, as seen at 117. It should be noted that for the purpose of this invention, the meaning of the term "suture" shall include any cord, string or filamentous material useful for tethering the housing 92 to the handle extension 94.

Handle extension 94 and housing 92 are fitted together by placing the tongue 116 into the groove 114. Sutures are run through aligned apertures to hold the handle extension 94 and housing 92 together. For example, one suture 134 is passed through apertures 126 and 127 of handle extension 94 and apertures 130 and 131 of housing 92, while a second suture 136 is passed through apertures 128 and 129 of handle extension 94 and apertures 132 and 133 of housing 92.

The handle assembly 90 of this embodiment is coupled to the guide mount assembly 18 as stated above. The handle post 96 is removed from the housing 92 by cutting the sutures 134 and 136 and pulling the handle extension 94 away from the housing 92. Pulling away the handle post 96 unravels the suture spool 106. After the suture guide is sutured into position along the suture line, i.e., about a heart valve annulus, the suture(s) holding the guide mount assembly to the suture guide is cut. The guide mount assembly is then removed by pulling on the handle post 96.

Figure 11:
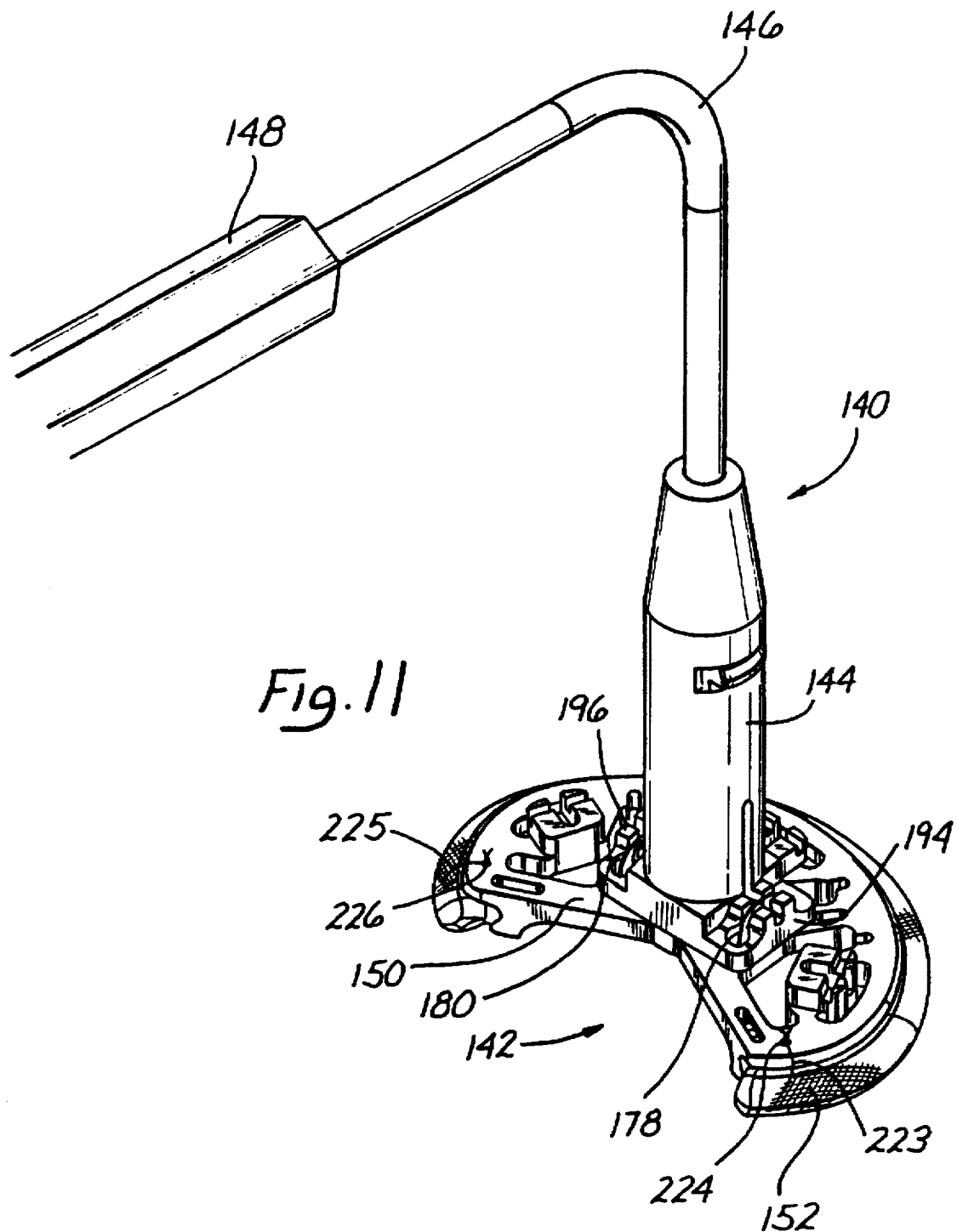
FIG. 11 is a perspective view of a suture guide holder in accordance with another embodiment of the invention.
Figure 12:
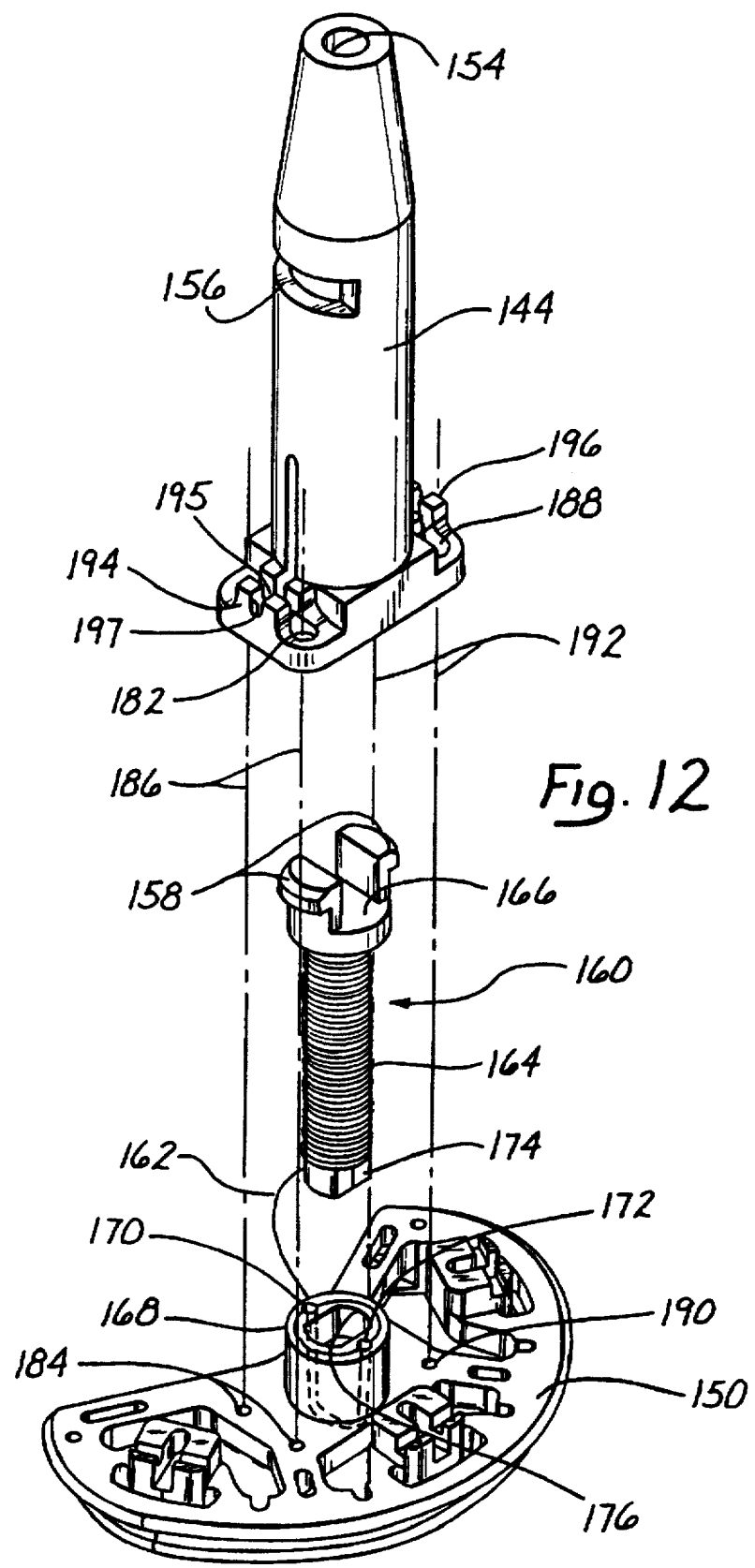
FIG. 12 is an exploded view of the guide mount portion and lower handle portion of the suture guide holder of FIG. 11.
Figure 13:
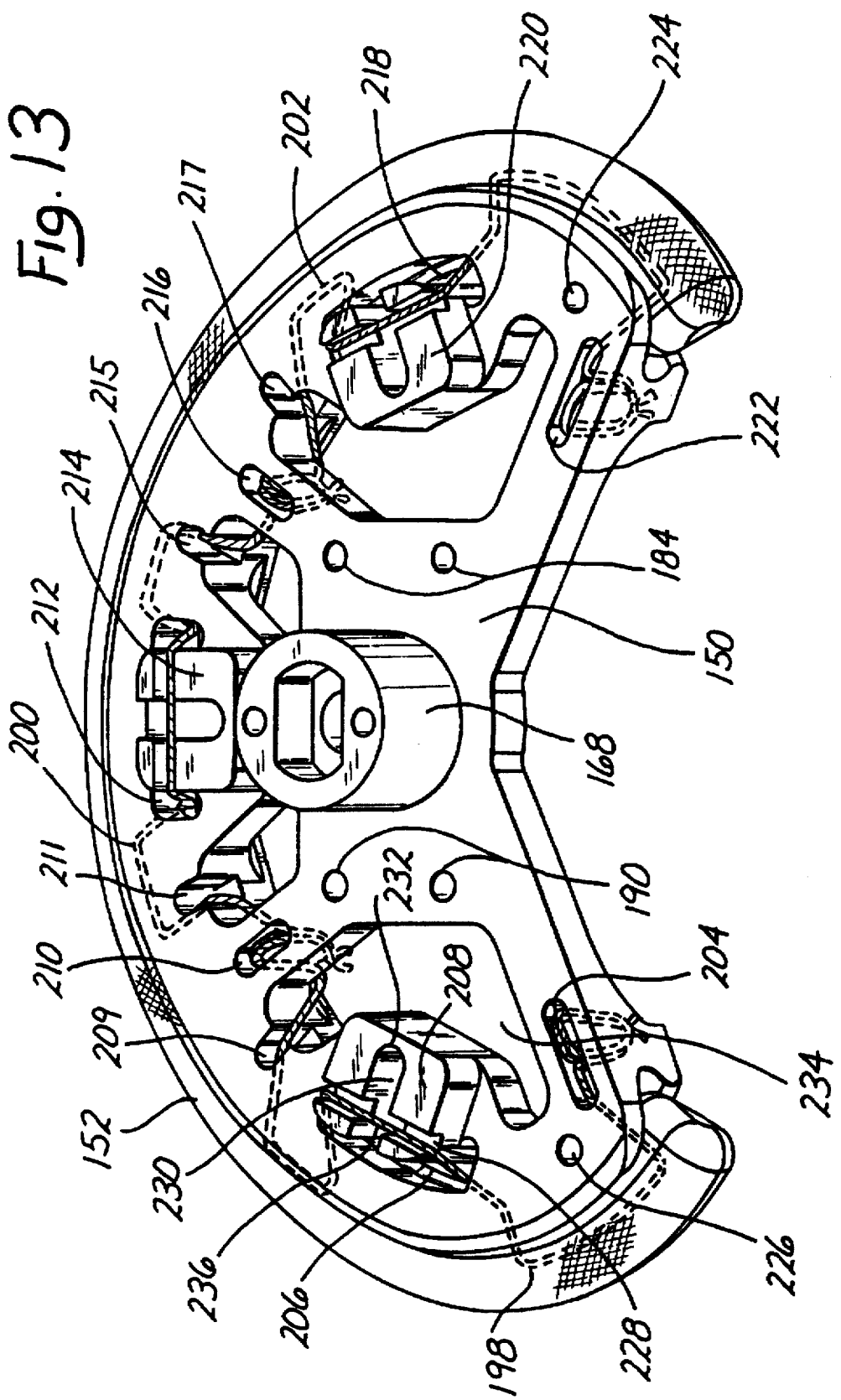
FIG. 13 is a top view of the guide mount portion of the suture guide holder of FIG. 11.

In another embodiment of the invention, shown in FIGS. 11–13, handle assembly 140 is also modified to house a spool of suture or string that acts like a tether for the guide mount assembly 142. Referring to FIG. 11, handle assembly 140, includes housing 144, handle post 146, and an enlarged handle portion 148. Handle post 146 is preferably made of a malleable metal or other material that allows the surgeon to bend the handle to the desired angle while using the suture guide holder assembly. The enlarged handle portion 148 allows the surgeon to grip the handle more easily and also makes it easier for the surgeon to maneuver the suture guide holder into the surgery site. Housing 144 is releasably attached to guide mount 150 as will be described in more detail with reference to FIG. 12. Suture guide 152 is releasably attached to guide mount 150 by threads or sutures (not shown) in a manner which will be described with reference to FIG. 13.

Referring to FIG. 12, housing 144 includes bore 154 for receiving handle post 146. The end of handle post 146 may be held in bore 154 by a press fit or friction fit, by welding, or by providing the respective members with interlocking threaded surfaces. Housing 144 also includes a pair of opposing slots 156 for receiving dog ears 158 of the suture spool 160. Suture spool 160 includes a length of suture or thread 162 wound into a cylindrical configuration along spindle post 164. One end of the suture 162 is tied to an aperture (not shown) in upper end 166 of suture spool 160. The other end of suture 162 is affixed to hub 168 of guide mount 150. Specifically, suture 162 passes down through aperture 170, up through aperture 172, and is tied off at aperture 172. The lower end of spindle post 164 has a pair of opposing notches 174 formed therein which are sized to be received by bore 176 of hub 168. Spindle post 164, therefore, is press fit or friction fit into bore 176.

Suture spool 160 is housed within the interior cavity (not shown) of housing 144 and is held in place when dog ears 158 snap fit into opposing slots 156. Housing 144 with suture spool 160 in place is then releasably attached to guide mount 150 by sutures or threads 178 and 180 shown in FIG. 11. Suture 180 passes through a pair of apertures 182 in housing 144 and a pair of apertures 184 in guide mount 150 as illustrated by dotted lines 186 in FIG. 12. Suture 178 passes through a pair of apertures 188 in housing 144 and a pair of apertures 190 in guide mount 150 as shown by dotted lines 192 in FIG. 12.

Once the suture guide and guide mount assembly has been placed at the surgery site, the surgeon can remove the handle if desired by cutting sutures or threads 178 and 180 at the location of the cutting guides 194 and 196 shown in FIGS. 11 and 12. Cutting guides 194 and 196 consist of a raised platform with a shallow groove 195 formed therein through which the suture passes and a deeper groove 197 formed in the platform perpendicular to the shallow groove through which scissors or other cutting tools can be inserted to clip or cut the suture at that location. When the sutures are cut and the handle is removed, spool 160 remains within housing 144 and suture 162 remains attached to hub 168. As the handle is pulled away from the guide mount, the suture or thread spools off spindle post 164 thereby providing a tether for removal of the guide mount after the suture guide has been detached from the guide mount and the surgery has been completed.

Referring to FIG. 13, suture guide 152 is releasably attached to guide mount 150 by sutures or threads 198, 200 and 202. Suture 198 is tied off at aperture 204 and then passes through one end of the suture guide and up through aperture 206 over cutting guide 208 down through aperture 206 again, through suture guide 152, through aperture 209, then up through aperture 210 where the other end of suture 198 is tied off. Suture 200 is at one end tied off through aperture 210 and then passes under the guide mount 150 through aperture 211, through suture guide 152 and up through aperture 212, across cutting guide 214 and back down through aperture 212. Suture 200 then passes through suture guide 152 again, through aperture 215 and up through aperture 216 where it is tied off. Finally, suture 202 is tied off at one end at aperture 216 and passes under suture guide 150 through aperture 217, through suture guide 152, up through aperture 218, across cutting guide 220, down through aperture 218 again where it passes through suture guide 152 and up through aperture 222 where it is tied off.

Apertures 224 and 226 disposed in guide mount 150 at opposite ends of the suture guide 152 are used to temporarily attach each end of suture guide 152 to each end of the guide mount 150 to hold the suture guide in place during the process of threading sutures 198, 200 and 202 through the apertures of the guide mount and the suture guide. Once the threading of sutures 198, 200 and 202 is complete, the sutures at 224 and 226 are then removed. The sutures at 224 and 226 are shown for illustration purposes in FIG. 11 at 223 and 225.

Referring to FIG. 13, cutting guides 208, 214 and 220 consist of a raised platform with a shallow groove 228 formed therein through which the suture passes and a deeper groove 230 formed in the platform perpendicular to the shallow groove through which a cutting tool may pass in order to cut the suture at the location lying over the deeper groove. The deeper groove is closed at one end by a stop 232 so that the tip of the cutting tool or scissors cannot pass beyond that point. This stop prevents the cutting tool from dipping down into the open space 234 between the spokes of guide mount 150 and accidentally cutting the tissue of the patient.

When the surgeon is ready to release the suture guide from the suture guide mount 150 he merely snips the sutures 198, 200 and 202 by passing the cutting tool into the cutting groove of the cutting guides. When the sutures have been snipped at all three locations, the guide mount can be retrieved by pulling on the tether or otherwise removing it and sutures 198, 200 and 202 are removed with the guide mount 150 since they are tied off on the guide mount.

Referring to FIGS. 14 through 18, there are shown two additional embodiments of suture guide holders for holding a suture guide. FIGS. 14 and 15 illustrate a linear suture guide holder for placing a linear suture guide. FIGS. 16, 17 and 18 illustrate a circular or ring-shaped suture guide holder for placing a circular suture guide.

Referring to FIG. 14, the linear suture guide holder has a detachable handle 240 of the type shown in FIG. 2 and linear-shaped guide mount 242. However, the handle embodiment with the tether illustrated in FIGS. 8 and 12 could also be used. Guide mount 242 has a linear groove or trough 244 into which suture guide 246 is fitted as shown in FIG. 15. Apertures 248 formed in guide mount 242 are used to suture the suture guide to the guide mount as shown in FIG. 15. Guide mount 242 also includes cutting guides 252 and 254 at each end of the guide mount.

Suture guide 246 is tautly secured to the linear guide mount 242 by suture 250. One end of suture 250 is tied off at aperture 248a, passes through suture guide 246 up through aperture 248b cross cutting guide 252 down through aperture 248c through suture guide 246 up through aperture 248d where it is tied to a second length of suture 256. Suture 256 is threaded down through aperture 248e through suture guide 246 up through aperture 248f across cutting guide 254 down through aperture 248g through suture guide 246 and up through aperture 248h where it is tied off. Thus, as in previous embodiments, when the surgeon is ready to release the suture guide from the suture guide holder, he merely inserts the cutting tool in the cutting grooves 252 and 254 and cuts sutures 250 and 256 at that location. Suture 250 and 256 are then removed with the suture guide mount 242. The linear suture guide shown in FIGS. 14 and 15 would be used for any surgical procedure in which the incision is a substantially straight line. The suture guide mount 242 can be any desired length and the suture guide 246 can extend the full length of the suture guide mount 242 as shown in FIG. 15 or could be of a shorter length and sutured to just a portion of suture guide mount 242. If the surgeon desires a suture guide with a hook or curved end, the suture guide could extend around the edge of suture guide mount 242 to provide one or two curved or hooked ends.

Referring to FIG. 16, there is shown a circular suture guide holder which would be useful for suturing two blood vessels or other vessels, such as intestines, together. It would also be useful for bowel and bronchial resection. The suture guide holder has a handle 260 which in this embodiment is not shown to be detachable. However, any of the various handle embodiments illustrated previously could be utilized, including the tethering concepts. The suture guide mount 258 is ring shaped with a groove or trough 260 formed on the interior cylindrical surface of the ring. The groove or trough 260 is shaped to receive a circular suture guide 261 as shown in FIG. 17. Suture guide mount 258 has a plurality of apertures 262 evenly spaced about its circumference for use in suturing the suture guide 261 to the suture guide holder as shown in FIG. 17. Suture 264 is threaded through the apertures and through the suture ring in a manner similar to that described with reference to FIGS. 14 and 15 and will not be further be described in connection with this embodiment. Suture 264 can be clipped at two locations such as at 266 and 268 in order release the suture guide from the suture guide holder. Alternatively, cutting guides can be provided as shown in the embodiments previously described and illustrated.

FIG. 18 shows a cross section of the suture guide holder with the suture guide attached thereto taken along line 18—18 of FIG. 17. FIG. 18 illustrates how groove 260 engages suture guide 261 and depicts rib 263 and the outer covering 265 of the suture guide.

Various shaped suture guide holders, C-shaped, linear and circular, have been described and illustrated in the figures, however, in accordance with the present invention, the suture guide holder can be constructed in any desired shape depending on the surgical procedure involved. For example, the suture guide holder could be curvilinear for stomach reduction surgery or for certain cosmetic surgeries when it is necessary to place a suture line along an eyelid or an ear.

While the preferred embodiments have been described, various modifications and substitutions may be made thereto without departing from the scope of the invention. Accordingly, it is to be understood that the invention has been described by way of illustration and not limitation.

What is claimed is:

1. A combination comprising:

a biocompatible freely flexible surgical suture guide of predetermined length;

a substantially annular rigid holder defined by opposed outer and inner annular surfaces, and a groove provided in the inner annular surface for holding the suture guide in a taut fashion along the length of the suture guide; and releasable retaining means associated with the holder for releasably holding the freely flexible suture guide in the taut fashion;

wherein, upon release of the suture guide from the holder by the releasable retaining means, the suture guide resumes flexibility.

2. The combination of claim 1 wherein the suture guide is fashioned from biocompatible biodegradable materials.

3. The combination of claim 1 wherein the suture guide is fashioned from non-biodegradable biocompatible materials suitable for permanent implant.

4. The combination of claim 3 wherein the surface of the suture guide encourages tissue ingrowth.

5. The combination of claim 1 wherein the suture guide comprises a flexible internal rib encased within a suturable covering.

6. The combination of claim 5 wherein the suturable covering is dacron velour.

7. The combination of claim 1 wherein the holder includes a handle coupled to the holder.

8. The combination of claim 7 further comprising a thread for coupling the handle to the holder, and wherein the handle comprises a cutting guide through which the thread passes, wherein a cutting tool may be inserted through the cutting guide to cut the thread to release the handle from the holder.

9. The combination of claim 1 wherein the inner annular surface of the holder has a shape selected to hold the length of the suture guide in a predetermined configuration.

10. The combination of claim 1 further comprising means for tethering a handle to the holder.

11. The combination of claim 10 wherein the tethering means comprises a lanyard having first and second ends, with one of the ends being connected to the handle and the other end being connected to the holder.

12. The combination of claim 10 wherein the releasable retaining means comprises at least a first thread having two opposing ends, each selectively affixed to the holder, with a portion of the thread being passed through a portion of the suture guide.

13. The combination of claim 10 wherein the tethering means comprises a spool of a length of filamentous material secured at one end to the holder and at an opposite end to the handle wherein the spool is housed within a cavity in the handle.

14. The combination of claim 10 wherein the tethering means comprises a length of filamentous material attached at one end to the holder and at an opposite end to the handle.

15. The combination of claim 1 wherein the releasable retaining means comprises at least a first thread having two opposing ends, each selectively affixed to the holder, with a portion of the thread being passed through a portion of the suture guide.

16. The combination of claim 15, wherein the holder further comprises a cutting guide through which the first thread passes, wherein a cutting tool may be inserted through the cutting guide to cut the first thread to release the suture guide from the holder.

17. The combination of claim 16 wherein the cutting guide comprises a raised platform provided on the holder, with a shallow groove formed in the platform through which the first thread passes and a deeper groove formed in the platform perpendicular to the shallow groove through which the cutting tool may pass to cut the first thread.

18. A combination comprising:

a biocompatible freely flexible surgical suture guide of predetermined length;

a rigid holder for holding the suture guide in a taut fashion along the said length;

a handle coupled to the holder;

releasable retaining means associated with the holder for releasably holding the freely flexible suture guide in the taut fashion, wherein the releasable retaining means comprises at least a first thread having two opposing ends, each selectively affixed to the holder, with a portion of the thread being passed through a portion of the suture guide;

a spool of a length of filamentous material secured at one end to the holder and at an opposite end to the handle wherein the spool is housed within a cavity in the handle; and wherein the holder further comprises a cutting guide through which the first thread passes, wherein a cutting tool may be inserted through the cutting guide to cut the first thread to release the suture guide from the holder.

19. The combination of claim 18 wherein the cutting guide comprises a raised platform provided on the holder, with a shallow groove formed in the platform through which the first thread passes and a deeper groove formed in the platform perpendicular to the shallow groove through which the cutting tool may pass to cut the first thread.

20. The combination of claim 18 wherein the suture guide is fashioned from biocompatible biodegradable materials.

21. The combination of claim 18 wherein the suture guide is fashioned from non-biodegradable biocompatible materials suitable for permanent implant.

22. The combination of claim 21 wherein the surface of the suture guide encourages tissue ingrowth.

23. The combination of claim 18 wherein the suture guide comprises a flexible internal rib encased within a suturable covering.

24. The combination of claim 23 wherein the suturable covering is dacron velour.

25. The combination of claim 18 wherein the handle is formed to be gripped during the placement of sutures through the suture guide.

26. The combination of claim 25 further comprising a thread for coupling the handle to the holder, and wherein the handle comprises a cutting guide through which the thread passes, wherein a cutting tool may be inserted through the cutting guide of the handle to cut the thread to release the handle from the holder.

27. The combination of claim 18 wherein the holder has an outer circumferential surface and a groove provided on the outer circumferential surface for holding the suture guide in a taut fashion along the said length of the suture guide.

28. The combination of claim 27 wherein the holder has a shape selected to hold the length of suture guide in a predetermined configuration.

29. The combination of claim 28 wherein the configuration is a predetermined circumference.

30. The combination of claim 28 wherein the configuration is at least a portion of a predetermined circumference.

31. The combination of claim 28 wherein the configuration is substantially linear and has a predetermined dimension.

32. The combination of claim 28 wherein the configuration is curvilinear and has a predetermined dimension.

* * * * *